United States Patent [19]
Quigley, Jr. et al.

[11] Patent Number: 6,075,056
[45] Date of Patent: Jun. 13, 2000

[54] ANTIFUNGAL/STEROID TOPICAL COMPOSITIONS

[75] Inventors: John W. Quigley, Jr.; Sui Yuen Eddie Hou, both of Foster City, Calif.; Bhaskar Chaudhuri, Cupertino, Calif.

[73] Assignee: Penederm, Inc., Foster City, Calif.

[21] Appl. No.: 08/943,574

[22] Filed: Oct. 3, 1997

[51] Int. Cl.⁷ .................................................. A01N 33/02
[52] U.S. Cl. .......................................................... 514/649
[58] Field of Search ............................................. 514/649

[56] References Cited

U.S. PATENT DOCUMENTS

| | | | |
|---|---|---|---|
| 4,282,251 | 8/1981 | Berney | 424/316 |
| 4,298,604 | 11/1981 | Hammell | 424/240 |
| 4,755,534 | 7/1988 | Stuetz | 514/655 |
| 4,912,124 | 3/1990 | Das et al. | 514/399 |
| 4,971,800 | 11/1990 | Chess et al. | 424/449 |
| 5,002,938 | 3/1991 | Wang et al. | 514/171 |
| 5,021,458 | 6/1991 | Maeda et al. | 514/655 |
| 5,045,317 | 9/1991 | Chess et al. | 424/401 |
| 5,051,260 | 9/1991 | Chess et al. | 424/449 |
| 5,106,866 | 4/1992 | Maeda et al. | 514/443 |
| 5,110,809 | 5/1992 | Wang et al. | 514/171 |
| 5,174,475 | 12/1992 | Day et al. | 222/144.5 |
| 5,219,877 | 6/1993 | Shah et al. | 514/399 |
| 5,310,545 | 5/1994 | Eisen | 424/49 |
| 5,407,663 | 4/1995 | Eisen | 424/49 |
| 5,506,354 | 4/1996 | McCall et al. | 540/5 |

FOREIGN PATENT DOCUMENTS

| | | | |
|---|---|---|---|
| 440298 A1 | 7/1991 | European Pat. Off. | A61K 7/04 |

OTHER PUBLICATIONS

Fukushiro et al., Butenafine HCl, A New Antifungal Agent, Recent Prog. Antifungal Chemother., Proc. Int. Conf., 1st, 147–57, 1990.

*Primary Examiner*—Jose' G. Dees
*Assistant Examiner*—Alton Pryor
*Attorney, Agent, or Firm*—Cooley Godward LLP

[57] ABSTRACT

Stable topical formulations comprising an antifungal agent and an antiinflammatory steroid are disclosed, useful for treating fungal diseases and their related inflammation.

26 Claims, No Drawings

ANTIFUNGAL/STEROID TOPICAL COMPOSITIONS

TECHNICAL FIELD

The invention relates to topical formulations useful for treating fungal diseases and their related inflammation. In particular, the invention relates to stable topical formulations comprising an antifungal agent and an antiinflammatory steroid.

BACKGROUND

Many methods are known for the topical treatment of fungal infections, including the use of antibiotics (e.g. nystatin and amphotericin B), imidazole antifungal agents such as miconazole, clotrimazole, econazole and sulconazole, and non-imidazole fungal agents such as the allylamine derivatives terbinafine and naftifine, and the benzylamine butenafine.

Recently, the combination of imidazole antifungal agents with a corticosteroid has been disclosed for the topical treatment of fungal diseases. The purpose of the steroid is to alleviate the symptoms of erythma and the related itching that are normally associated with fungal infections. Additionally, steroids may also induce fungal spores to be more sensitive to treatment by an antifungal agent.

However, the disadvantage of such a combination is that it is undesirable to use steroids for topical treatment for extended periods of time. Steroids can penetrate the skin and cause undesirable side effects, including skin atrophy, suppression of the hypothalamic-pituitary-adrenal axis, Cushing's syndrome, glucosuria, hyperglycemia, etc. Additionally, the addition of a steroid may actually decrease the effectiveness of some antifungal compounds, because of the potential of steroids to function as a deactivating agent. Additionally, some antifungal compounds are quite toxic in their own right.

Currently, the commercially available products that contain a mixture of an antifungal and a steroid are Lotrisone cream (clotrimazole 1%/betamethasone dipropionate 0.064%), Daktacort cream (miconazole nitrate 2%/hydrocortisone 1%) and Canesten HC cream (clotrimazole 1%/hydrocortisone 1%). However, as a consequence of the prolonged time necessary to effect successful treatment, these products exhibit the undesirable side effects noted above.

It would therefore be advantageous to have a formulation that retains the advantages of combining an agent useful for treating fungal diseases with a steroid capable of reducing the associated inflammation, with the ability to rapidly eradicate fungal infections and eliminate the symptoms thereof, and as a consequence minimize the risk of undesirable side effects. Such a formulation would ideally deliver the antifungal agent and the steroid to the skin, and maintain the combination on the skin for the period of time necessary to effect treatment, but minimize the penetration of the skin with respect to the active ingredients, thus avoiding the potential steroid side effects noted above. Surprisingly, we have discovered such a formulation.

Relevant Literature

Combinations of antifungals and steroids are disclosed in U.S. Pat. Nos. 4,912,124, 5,002,938, 5,021,458, 5,110,809, 5,174,475, 5,219,877, 5,407,663, and 5,310,545,

SUMMARY OF THE INVENTION

The present invention relates to topical formulations useful in the treatment of fungal diseases. In particular, the invention relates to stable topical formulations comprising a non-imidazole bearing antifungal agent (i.e. lacking an imidazole functional group within the molecule), including benzylamine-containing antifungal agents, for example butenafine, or allylamine-containing antifungal agents such as terbinafine, naftifine, and the like. The topical formulation also comprises an antiinflammatory steroid, for example betamethasone, betamethasone dipropionate, fluocinonide, fluocinolone acetonide, hydrocortisone, methylprednisolone, clobetasol, beclomethasone, and the like. The combination has unexpected advantages in that for those formulations that contain an ester-bearing steroid group, the ester is hydrolysed at a much lower rate that expected by the components of the topical formulation, thus providing increased shelf life for the formulation. Additionally, the combination of the antifungal agent and the steroid demonstrates a synergistic effect, in that antifungal activity is unexpectedly superior to that shown by the antifungal in the absence of the steroid. As a consequence, the time is greatly reduced for alleviation of the symptoms and for complete eradication of the disease as compared to the use of the antifungal agent in the absence of a steroid, or to known steroid/antifungal combinations. Another advantage of the formulation is that it delivers the antifungal agent and the steroid to the skin, but minimizes the penetration of the skin with respect to the steroid, thus avoiding the potential side effects attendant upon prolonged steroid use.

In particular, the invention relates to a topical antifungal composition comprising:
a) a therapeutically effective amount of an antifungal compound of Formula I:

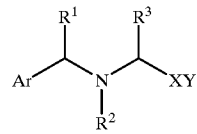

Formula I wherein:
$R^1$, $R^2$, and $R^3$ are independently hydrogen or lower alkyl;
X is —CH═CH— or —$(CH_2)_n$—;
  in which n is 0, 1 or 2;
Y is —C≡C—$R^4$, aryl, or heteroaryl;
  in which $R^4$ is lower alkyl; and
Ar is aryl or heteroaryl;
or a pharmaceutically acceptable salt thereof;
b) a therapeutically effective amount of an antiinflammatory steroid; and
c) pharmaceutically acceptable excipients sufficient to form a topical composition.

The pharmaceutically acceptable excipients are chosen from a mixture of solvents, emollients, humectants, and emulsifiers. Solvents may be propylene glycol, butylene glycol, hexylene glycol, polyethylene glycols, polypropylene glycols, polyurethane compounds, including hydroxy-terminated polyurethanes, in particular polyolprepolymer-2, polyolprepolymer-14, or polyolprepolymer-15. Emollients may be white petrolatum, mineral oil, propylene glycol dicaprylate, lower fatty acid esters and lower alkyl ethers of propylene glycol, cetyl alcohol, cetostearyl alcohol, stearyl alcohol, cetyl esters wax, spermaceti wax, and white wax. Humectants may be glycerin and sorbitol; and emulsifiers may be glyceryl monostearate, glyceryl monoleate, polyoxyethylene cetyl ether, polyoxyethylene cetostearyl ether, polyoxyethylene stearyl ether, and polyethylene glycol stearate. The pH is adjusted where necessary to a pH of about 3.5–7.0, using an acid e.g. hydrochloric acid phosphoric acid, or a base e.g. diethanolamine, triethanolamine, sodium hydroxide, or known buffering agents, e.g. phosphates such as monobasic sodium phosphate, and dibasic sodium phosphate, and citrates well known in the art. A preservative is generally present, for example benzyl alcohol, sodium benzoate, parabens, and the like.

Another aspect of the invention is a method of treating fungal diseases by application to the skin of a mammal the claimed topical compositions.

Another aspect of the invention is an article of manufacture comprising the claimed topical compositions in combination with labeling instructions for application of the topical compositions in the treatment of fungal diseases.

DESCRIPTION OF SPECIFIC EMBODIMENTS

Definitions

As used herein:

"Alkyl" means a branched or unbranched saturated monovalent hydrocarbon radical containing 1 to 12 carbon atoms, such as methyl, ethyl, propyl, isopropyl, tert-butyl, butyl, n-hexyl, dodecyl, and the like, unless otherwise indicated.

"Lower alkyl" means a branched or unbranched saturated monovalent hydrocarbon radical containing 1 to 6 carbon atoms, such as methyl, ethyl, propyl, isopropyl, tert-butyl, butyl, n-hexyl and the like, unless otherwise indicated.

"Lower alkoxy" means the group —O—(lower alkyl) wherein lower alkyl is as herein defined. "Lower alkyl ethers of propylene glycol" refers to compounds of the formula (lower alkyl)—O—CH$_2$—CH$_2$(CH$_3$)—O—(lower alkyl). "Lower fatty acid esters of propylene glycol" refers to compounds of the formula (lower alkyl)—C(O)O—CH$_2$—CH$_2$(CH$_3$)—OC(O)—(lower alkyl).

"Alkylene" means a branched or unbranched saturated divalent hydrocarbon radical containing 1 to 12 carbon atoms, such as methylene, ethylene, 1,2-propylene, 1,4-butylene, 1,3-butylene, 1,5-pentylene, 1,3-pentylene, 1,6-hexylene, 1,12-docecylene, and the like.

"Alkenylene" means a branched or unbranched unsaturated divalent hydrocarbon radical containing 2 to 12 carbon atoms, such as ethene, 1-propene, 1-butene, 3-methylbut-1-ene, 1-pentene, 2-methylpent-1-ene, 1-hexene, 1-docecene, and the like.

"Halo" means fluoro, chloro, bromo, or iodo.

The term "aryl" refers to a monovalent unsaturated aromatic carbocyclic radical having a single ring (e.g., phenyl) or two rings (e.g., naphthyl, biphenyl, indanyl, 1,2,3,4-tetrahydronaphthyl, benzocycloheptane), which can optionally be mono-, di- or tri-substituted, independently, with OH, COOH, lower alkyl, lower alkoxy, halo, nitro, amino, alkylamino, dialkylamino, trifluoromethyl and/or cyano.

The term "heteroaryl" refers to a monovalent aromatic carbocyclic radical having 1–3 heteroatoms within one or two rings, (e.g., thiophenyl, furanyl, pyridyl, thiazolyl, pyrimidine, oxazolyl, benzoxazole, benzofuran, benzothiophene, indolinyl, quinoline), which can optionally be mono-, di- or tri-substituted, independently, with OH, COOH, lower alkyl, lower alkoxy, halo, nitro, amino, alkylamino, dialkylamino, trifluoromethyl and/or cyano.

The term "heteroatom" refers to oxygen, sulfur and nitrogen, unless otherwise specified.

The topical compositions of the present invention include antifungal compounds lacking an imidazole functional group within the molecule. The antifungal agents of particular interest have a structure that includes a benzylamine moiety, for example butenafine, are disclosed in U.S. Pat. Nos. 5,021,458 and 5,106,866, or include an allylamine moiety, for example naftifine and terbinafine, are disclosed in U.S. Pat. Nos. 4,282,251 and 4,755,534, each of which is incorporated by reference. Antifungals of particular interest include, but are not limited to, terbinafine, naftifine, and butenafine.

Terbinafine is a compound of Formula I wherein Ar is 1-naphthyl, R$^1$ is hydrogen, R$^2$ is methyl, R$^3$ is hydrogen, X is —CH=CH—, and Y is —C≡C—R$^4$, in which R$^4$ is t-butyl, and has the structure:

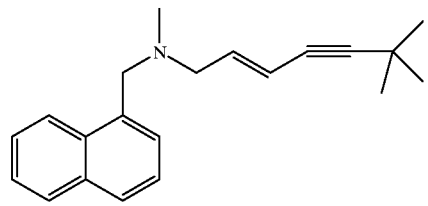

Naftifine is a compound of Formula I wherein Ar is 1-naphthyl, R$^1$ is hydrogen, R$^2$ is methyl, R$^3$ is hydrogen, X is —CH=CH—, and Y is phenyl, and has the structure:

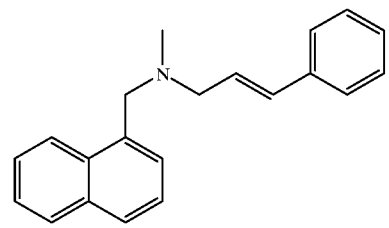

Butenafine is a compound of Formula I wherein Ar is 1-naphthyl, R$^1$ is hydrogen, R$^2$ is methyl, R$^3$ is hydrogen, X is —(CH$_2$)$_n$— in which n is 0, and Y is 4-(t-butyl)phenyl, and has the structure:

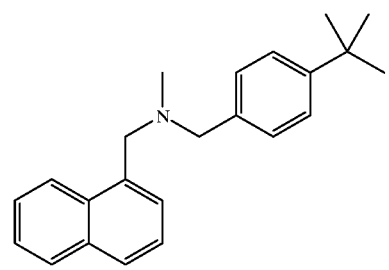

The topical compositions of the present invention include antiinflammatory steroids. Such steroids are exemplified in, but not limited to, the following table:

1 Betamethasone dipropionate cream, ointment 0.05% (optimized vehicle)
  Clobetasol propionate cream, ointment 0.05% (optimized vehicle)
  Diflorasone diacetate ointment 0.05% (optimized vehicle)
  Halbetosal propionate cream, ointment 0.05%
2 Amicinonide ointment 0.1%
  Betamethasone dipropionate cream 0.05%
  Betamethasone dipropionate ointment 0.05%
  Desoximetasone cream, ointment 0.25%
  Desoximetasone gel 0.05%
  Diflorasone diacetate ointment 0.05%

Fluocinonide cream, gel, ointment (0.05%)
Halcinonide 0.1% cream
Mometasone furoate ointment 0.1%
Triamcinolone acetonide ointment 0.5%
3 Amicinonide cream, lotion 0.1%
  Betamethasone benzoate gel 0.025%
  Betamethasone 0.05%
  Betamethasone dipropionate cream 0.05%
  Betamethasone valerate ointment 0.1%
  Diflorasone diacetate cream 0.05%
  Fluticasone propionate ointment, 0.005%
  Fluocinonide cream 0.05%
  Halocinonide ointment 0.1%
  Triamcinolone acetate ointment 0.1%
4 Betamethasone benzoate ointment 0.025%
  Betamethasone valerate lotion 0.1%
  Desoximetasone cream 0.05%
  Fluocinolone acetonide cream 0.2%
  Fluocinolone acetonide ointment 0.025%
  Flurandrenolide ointment 0.05%
  Halcinonide cream 0.025%
  Hydrocortisone valerate ointment 0.2%
  Mometasone furoate cream 0.1%
  Triamcinolone acetonide ointment 0.1%
5 Betamethasone benzoate cream 0.025%
  Betamethasone dipropionate lotion 0.02%
  Betamethasone valerate cream 0.1%
  Clocortalone cream 0.1%
  Fluocinolone acetonide cream 0.025%
  Fluocinolone acetonide oil 0.01%
  Flurandrenolide cream 0.05%
  Fluticasone propionate cream 0.05%
  Hydrocortisone butyrate cream 0.1%
  Hydrocortisone valerate cream 0.2%
  Predincarbate 0.1% cream
  Triamcinolone acetonide cream 0.25%
6 Aclometasone dipropionate cream, ointment 0.05%
  Betamethasone valerate lotion 0.1%
  Desonide cream 0.05%
  Fluocinolone acetonide cream solution 0.01%
  Triamcinolone acetonide cream, lotion 0.1%
7 Dexamethasone cream 0.1%
  Hydrocortisone 0.5%, 1.0, 2.5%
  Methylprednisolone 1%

The table lists the steroids in decreasing potency, i.e. highest potency in category 1, lowest potency in category 7. The amount of steroid required for a therapeutically effective amount will vary depending upon its potency, i.e. the more potent the steroid the less needed, and vice versa. The total amount of steroid present may vary from about 0.001% to about 5%, preferably about 0.01–1%.

Preferred antiinflammatory steroids include betamethasone, betamethasone dipropionate, fluocinonide, fluocinolone acetonide, hydrocortisone, methylprednisolone, clobetasol, and beclomethasone.

One pharmaceutically acceptable excipient optionally present in this invention is identified as a "polyurethane compound". This description is intended to include any conventional polyurethane compound formed by reaction of a diisocyanate with a compound having an active hydrogen, for example as disclosed in U.S. Pat. No. 4,079,028. A compound having an active hydrogen includes alcohols, diols, triols, amines, hydroxy-terminated polyesters, silanols, carboxylic acids, and the like. More particularly, the definition of "polyurethane compound" includes compounds which have the formula:

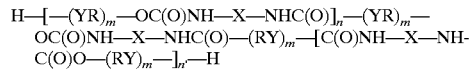

wherein:
X is an alkylene or alkenylene radical containing from 1 to about 20 carbon atoms, or a cycloalkylene or cycloalkenylene radical containing from about 5 to 20 carbon atoms, or a mononuclear or fused ring arylene radical containing from about 6 to about 10 carbon atoms, unsubstituted or substituted with one or more lower alkyl, lower alkoxy, lower alkoxy-substituted lower alkyl, nitro or amino groups or halogen atoms;
Y is oxygen, sulfur, silicon, or —NH—;
R is the same or different, and is chosen from alkylene, alkenylene, —SiR$^2$R$^3$—, and —CR$^2$R$^3$—NR$^4$—CR$^2$R$^3$—, wherein R$^2$, R$^3$ and R$^4$ are independently hydrogen or lower alkyl;
m is an integer selected to provide a (YR) moiety having a molecular weight of from about 40 to about 6,000; and
n and n' are the same or a different integer from 0–30 inclusive, correlated with m so as to provide a polyurethane compound having a molecular weight of up to about 200,000.

Polyurethane compounds where YR is —SiR$^2$R$^3$— or —CR$^2$R$^3$—NR$^4$—CR$^2$R$^3$— are well known in the art. Preferred are polyurethanes that are hydroxy-terminated polyurethanes, i.e. where Y is oxygen, especially those where R is alkylene or alkenylene, which are disclosed in U.S. Pat. Nos. 4,971,800, 5,045,317, and 5,051,260, the complete disclosures of which are hereby incorporated by reference.

A preferred hydroxy-terminated polyurethane has the above formula where X is 4,4'-dicyclohexylmethane, Y is oxygen, R is 1,2-propylene, m is 1–4, n and n' are both 12. It has a tradename of polyolprepolymer-2, and is prepared by the reaction of 2 moles of polypropylene glycol and 1 mole of dicyclohexylmethane diisocyanate in the presence of stannous octoate, as detailed in U.S. Pat. No. 4,971,800, Examples 1 and 5. It has a CAS# 9042-82-4, and a CAS name poly[oxy(methyl-1,2-ethanediyl)], α-hydro-ω-hydroxy-, polymer with 1,1'-methylene-bis-[4-isocyanatocyclohexane]. Also preferred is polyolprepolymer-14, which has the same CAS# and name, but a higher molecular weight (a weight average molecular weight of 14,000 as opposed to 4,000 for polyolprepolymer-2), and polyolprepolymer-15, which has a CAS# 39444-87-6, and is named poly(oxy-1,2-ethanediyl), α-hydro-ω-hydroxy-, polymer with 1,1'-methylene-bis-[4-isocyanatocyclohexane].

"Optional" or "optionally" means that the subsequently described event or circumstance may or may not occur, and that the description includes instances where said event or circumstance occurs and instances in which it does not. For example, "optionally substituted phenyl" or "optionally substituted naphthyl" means that the phenyl or naphthyl may or may not be mono-, di- or tri-substituted, independently, with OH, COOH, lower alkyl, lower alkoxy, halo, nitro, amino, and trifluoromethyl, and that the description includes both unsubstituted phenyl and naphthyl and substituted phenyl and naphthyl.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e. arresting its development; and (iii) relieving the disease, i.e. causing regression of the disease.

The term "therapeutically effective amount" refers to that amount which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art. Thus, a therapeutically amount of an antifungal is that amount which is sufficient to effect treatment, as defined above, when administered to a mammal in need of treatment by an antifungal agent. A therapeutically amount of an antiinflammatory steroid is that amount which is sufficient to effect treatment, as defined above, when administered to a mammal in need of treatment by an antiinflammatory steroid.

The term "fungal diseases" refers to any fungal infections (including yeast infections) of keratinized and non-keratinized epithelial tissues, for example skin, nails, mucosa, and the like, and includes tinea pedis, tinea capitis, tinea corporis, tinea versicolor, nail fungal diseases, scalp disorders, tinea cruris, and candidiasis.

The topical formulations of the invention may be provided as creams, ointments, gels, lotions, foams, powders, shampoos, liquid solutions, and the like. Powders and liquid solutions may also be formulated as aerosols or sprays. Examples of such formulations are shown below.

The cream formulation according to this invention can have the composition shown in Table A.

TABLE A

| Ingredients | Concentration Wt % | |
|---|---|---|
| | Operable | Preferred |
| Water | qs | qs |
| Glycerin | 2–10 | 5–10 |
| Glyceryl monostearate, self emulsifying type | 1–10 | 2–5 |
| White petrolatum | 1–10 | 4–8 |
| Propylene glycol | 5–20 | 5–15 |
| Propylene glycol dicaprylate | 5–20 | 5–15 |
| Cetyl alcohol | 1–10 | 4–8 |
| Stearic acid | 1–10 | 3–6 |
| Polyolprepolymer-2 | 0–10 | 1–3 |
| Polyoxyethylene cetyl ether | 1–10 (n = 20–24) | 2–5 (n = 23) |
| Benzyl alcohol | 0.5–3 | 0.5–1.5 |
| Sodium benzoate | 0–0.5 | 0.2–0.4 |
| Steroid | 0.01–2.5 | 0.01–0.1 |
| Antifungal | 0.5–5 | 1–3 |

An acid such as hydrochloric acid or a base such as diethanolamine, triethanolamine (trolamine), or sodium hydroxide is used to adjust the pH to between 3.5 to 7.0. Alternatively, a buffering agent such as monobasic or dibasic sodium phosphate with sodium hydroxide or phosphoric acid can be used for pH adjustment.

White petrolatum is an emollient cream base and can be replaced by mineral oil.

Propylene glycol is a solvent and can be replaced by butylene glycol, hexylene glycol, polyethylene glycols, or polypropylene glycols.

Propylene glycol dicaprylate is a solvent/emollient and can be replaced by lower fatty acid esters or lower alkyl ethers of propylene glycol.

Glycerin is a humectant/emollient and can be replaced by sorbitol.

Glyceryl monostearate, self emulsifying type, is an emulsifier and can be replaced by glyceryl monoleate, self emulsifying type.

Polyoxyethylene cetyl ether is an emulsifier and can be replaced by polyoxyethylene cetostearyl ether, polyoxyethylene stearyl ether, or polyethylene glycol stearates.

Cetyl alcohol is an emollient and a emulsion stabilizer/viscosity increasing agent in the cream and can be replaced by cetostearyl alcohol, stearyl alcohol, cetyl esters wax, spermaceti wax or white wax.

Polyolprepolymer-2 is a solvent/emollient and can be replaced by polyolprepolymer-14, or polyolprepolymer-15.

Sodium benzoate is a preservative and can be replaced by or used in conjunction with benzyl alcohol or parabens, or other commonly used preservatives.

Stearic acid is present as an emulsifier and a viscosity enhancer.

The steroids suitable for this invention are described in the Summary of the Invention; preferred is betamethasone dipropionate.

The antifungals suitable for this invention are described in the Summary of the Invention; preferred is butenafine, more preferably as the hydrochloride salt.

The cream formulation according to this invention can also have the composition shown in Table B.

TABLE B

| Ingredients | Concentration Wt % | |
|---|---|---|
| | Operable | Preferred |
| Water | qs | qs |
| White petrolatum | 1–20 | 5–10 |
| Propylene glycol | 2–20 | 3–15 |
| Cetearyl alcohol | 1–10 | 3–8 |
| Polyolprepolymer-2 | 0–10 | 1–3 |
| Stearic acid | 0–10 | 3–6 |
| Mineral oil | 5–20 | 5–10 |
| Ceteareth-30 | 1–10 | 2–8 |
| Benzyl alcohol | 0.5–3 | 0.5–1.5 |
| Steroid | 0.01–2.5 | 0.01–0.1 |
| Antifungal | 0.5–5 | 1–3 |

A buffering agent such as monobasic or dibasic sodium phosphate with sodium hydroxide or phosphoric acid is added to achieve a final pH between 3.5 and 7.0.

White petrolatum is an emollient cream base and can be replaced by mineral oil.

Propylene glycol is a solvent and can be replaced by butylene glycol or hexylene glycol, polyethylene glycols, polypropylene glycols.

Ceteareth-30 is an emulsifying agent and can be replaced by ceteareth-20, steareth-20, or steareth-30.

Polyolprepolymer-2 is a solvent/emollient and can be replaced by polyolprepolymer-14, or polyolprepolymer-15.

The steroids suitable for this invention are described in the Summary of the Invention; preferred is betamethasone dipropionate.

The antifungals suitable for this invention are described in the Summary of the Invention; preferred is butenafine, more preferably as the hydrochloride salt.

The above creams are prepared using standard techniques for preparing creams of the oil-in-water emulsion type. The drugs are dissolved in the oil phase consisting of melted oil-soluble components of the formulation prior to addition of this phase to the aqueous phase. The emulsion is then homogenized.

Another cream formulation is shown in Table C.

TABLE C

| Ingredients | Concentration Wt % | |
|---|---|---|
| | Operable | Preferred |
| Water | qs | qs |
| Cetyl alcohol | 1–10 | 2–5 |
| Stearyl alcohol | 1–10 | 2–5 |
| Isopropyl myristate | 1–10 | 5–10 |
| Cetyl palmitate | 1–20 | 1–10 |
| Polysorbate 60 | 1–15 | 1–10 |
| Sorbitan monostearate | 1–15 | 1–10 |
| Stearic acid | 0–10 | 1–6 |
| Polyolprepolymer-2 | 0–10 | 0–3 |
| Benzyl alcohol | 0.5–3 | 0.5–1.5 |
| Steroid | 0.01–2.5 | 0.01–0.1 |
| Antifungal | 0.5–5 | 1–3 |

An acid such as hydrochloric acid or a base such as diethanolamine, triethanolamine (trolamine), or sodium hydroxide is used to adjust the pH to between 3.5 to 7.0. Isopropyl myristate is a solvent/emollient and isopropyl palmitate may be used in its place.

Cetyl palmitate is an emollient and an emulsion stabilizer/viscosity increasing agent and can be replaced by cetyl esters wax or its various ester components, spermaceti wax, or a white wax.

Polysorbate 60 is a hydrophilic nonionic surfactant and is used as an emulsifier. Polysorbate 80 or other suitable polysorbates may be used in its place.

Sorbitan monostearate is a lipophilic nonionic surfactant and is used as an emulsifier.

Sorbitan palmitate or other sorbitan fatty acid esters may be used in its place.

The gel vehicle according to this invention can have the composition shown in Table D.

TABLE D

| Ingredients | Concentration Wt % | |
|---|---|---|
| | Operable | Preferred |
| Water | qs | qs |
| Ethanol | 10–80 | 20–60 |
| Propylene glycol | 3–20 | 5–10 |
| Glycerin | 5–20 | 5–10 |
| Polyolprepolymer-2 | 0–10 | 1–3 |
| Hydroxypropyl cellulose | 0.5–3 | 0.5–2 |
| Steroid | 0.01–2.5 | 0.01–0.1 |
| Antifungal | 0.5–10 | 1–8 |

An acid such as hydrochloric acid or a base such as diethanolamine, triethanolamine (trolamine), or sodium hydroxide is used to adjust the pH to between 3.5 to 7.0. Alternatively, buffering agents such as monobasic or dibasic sodium phosphate with sodium hydroxide or phosphoric acid or citric acid in combination with dibasic sodium phosphate can be used to adjust the pH.

Isopropyl alcohol can be used in place of ethanol.

Propylene glycol is a solvent and can be replaced by butylene glycol, hexylene glycol, polyethylene glycols, or polypropylene glycols.

Glycerin is a humectant/emollient and can be replaced by sorbitol.

Polyolprepolymer-2 is a solvent/emollient and can be replaced by polyolprepolymer-14, or polyolprepolymer-15.

The steroids suitable for this invention are described in the Summary of the Invention; preferred is betamethasone dipropionate.

The antifungals suitable for this invention are described in the Summary of the Invention; preferred is butenafine, more preferably as the hydrochloride salt.

Gels are prepared by dissolving the antifungal and steroid in the non-aqueous solvents followed by the addition of polyolprepolymer. If necessary, the base or the buffer (in solution) is added to the above solution with mixing to achieve the desired pH. The hydroxypropyl cellulose is then dispersed into the solution.

Another gel vehicle according to this invention can have the composition shown in Table E.

TABLE E

| Ingredients | Concentration Wt % | |
|---|---|---|
| | Operable | Preferred |
| Water | qs | qs |
| Ethanol | 10–80 | 20–60 |
| Polysorbate 80 | 1–10 | 2–8 |
| Carbomer 934P | 0.5–3 | 0.5–2 |
| Edetate disodium | 0.005–0.1 | 0.01–0.1 |
| Steroid | 0.01–2.5 | 0.01–0.1 |
| Antifungal | 0.5–10 | 1–8 |

A base such as diisopropanolamine, diethanolamine, triethanolamine (trolamine), or sodium hydroxide is used to adjust the pH to between 3.5 to 7.0.

Isopropyl alcohol may be used instead of ethanol as a solvent.

Polysorbate 80 is a nonionic surfactant and is used as a solubilizer. Another suitable polysorbate or a suitable polyoxyethylene alkyl ether may be used in its place.

Edetate disodium is a chelating agent/antioxidant and edetic acid and its various sodium salts can be used in its place.

The ointment formulation according to this invention can have the composition shown in Table F.

TABLE F

| Ingredients | Concentration Wt % | |
|---|---|---|
| | Operable | Preferred |
| White petrolatum | qs | qs |
| Ethanol | 0–20 | 0–5 |
| Propylene glycol | 5–25 | 10–15 |
| Polyolprepolymer-2 | 0–10 | 1–3 |
| Glyceryl stearate | 1–8 | 3–5 |
| Steroid | 0.01–2.5 | 0.01 to 0.1 |
| Antifungal | 0.5–5 | 1–3 |

Propylene glycol is a solvent and can be replaced by butylene glycol or hexylene glycol, polyethylene glycols, or polypropylene glycols.

Propylene glycol stearate or glyceryl oleate may be used in place of glyceryl stearate as an emulsifier.

The steroids suitable for this invention are described in the Summary of the Invention; preferred is betamethasone dipropionate.

The antifungals suitable for this invention are described in the Summary of the Invention; preferred is butenafine, more preferably as the hydrochloride salt.

The ointment is prepared by dissolving the antifungal and steroid in the solvent or solvent mixture, which is then added to the melted petrolatum and emulsifier with mixing. The preparation is then allowed to cool with continued mixing. Further mixing with a homogenizer may be done.

The lotion formulation according to this invention can have the composition shown in Table G.

TABLE G

| | Concentration Wt % | |
|---|---|---|
| Ingredients | Operable | Preferred |
| Water | qs | qs |
| Propylene glycol | 3–20 | 5–10 |
| Glycerin | 2–10 | 3–5 |
| Propylene glycol dicaprylate | 1–15 | 3–10 |
| Glyceryl monostearate, self emulsifying type | 1–5 | 2–3 |
| Polyoxyethylene cetyl ether | 1–5 (n = 20–24) | 2–3 (n = 23) |
| Stearic acid | 1–3 | 1–2 |
| Cetyl alcohol | 0.5–3 | 0.5–2 |
| White petrolatum | 0–5 | 1–2 |
| Polyolprepolymer-2 | 0–10 | 1–3 |
| Benzyl alcohol | 0.5–3 | 0.5–1.5 |
| Sodium benzoate | 0–0.5 | 0.2–0.4 |
| Magnesium aluminum silicate | 0.3–1 | 0.5–0.8 |
| Xanthan gum | 0.1–0.5 | 0.2–0.3 |
| Steroid | 0.01–2.5 | 0.01 to 0.1 |
| Antifungal | 0.5–5 | 1 to 3 |

An acid such as hydrochloric acid or a base such as diethanolamine, triethanolamine (trolamine), or sodium hydroxide is used to adjust the pH to between 3.5 to 7.0. Alternatively, a buffering agent such as monobasic or dibasic sodium phosphate with sodium hydroxide or phosphoric acid can be used for pH adjustment.

The materials may be substituted as shown in the cream formulation of Table A.

The steroids suitable for this invention are described in the Summary of the Invention; preferred is betamethasone dipropionate.

The antifungals suitable for this invention are described in the Summary of the Invention; preferred is butenafine, more preferably as the hydrochloride salt.

These lotions are prepared using standard techniques for formulating a lotion of oil-in-water emulsion type. The antifungal and steroid are dissolved in the melted oil phase, which is added to the aqueous phase in which the thickeners, magnesium aluminum silicate and xanthan gum, are already dispersed. The mixture is then homogenized.

The liquid solution formulation according to this invention can have the composition shown in Table H.

TABLE H

| | Concentration Wt % | |
|---|---|---|
| Ingredients | Operable | Preferred |
| Water | qs | qs |
| Ethanol | 10–80 | 20–60 |
| Polyethylene glycol 400 | 5–30 | 5–10 |
| Propylene glycol | 0–20 | 5–10 |
| Glycerin | 0–10 | 5–8 |
| Polyolprepolymer-2 | 0–10 | 1–3 |
| Steroid | 0.01–2.5 | 0.01 to 0.1 |
| Antifungal | 0.5–5 | 1–3 |

An acid such as hydrochloric acid or a base such as diethanolamine, triethanolamine (trolamine), or sodium hydroxide can be used to adjust the pH to between 3.5 to 7.0. Alternatively, buffering agents such as monobasic or dibasic sodium phosphate with sodium hydroxide or phosphoric acid or a combination of citric acid with dibasic sodium phosphate can be used to adjust the pH.

Isopropyl alcohol can be used in place of ethanol.

Sorbitol can be used in place of glycerin.

Polyolprepolymer-2 is a solvent/emollient and can be replaced by polyolprepolymer-14, or polyolprepolymer-15.

The steroids suitable for this invention are described in the Summary of the Invention; preferred is betamethasone dipropionate.

The antifungals suitable for this invention are described in the Summary of the Invention; preferred is butenafine, more preferably as the hydrochloride salt.

These liquid solutions are prepared by dissolving the antifungal and steroid in the nonaqueous solvents followed by addition of the polyolprepolymer and mixing. If necessary, the base or the buffer (in solution) is added to the above solution with mixing to achieve the desired pH.

The liquid solution formulation can be used as a spray as is or as an aerosol with the addition of suitable propellants, for example hydrocarbon gases or low boiling liquids, or standard compressed gases, for example carbon dioxide.

In general, the method of treating a fungal disease is carried out by topically applying the compositions of this invention in an amount sufficient for treatment. The amount used should be equivalent to clinical levels. Preferred amounts are between 2–10 mg/cm$^2$ The time necessary for resolution of certain symptoms of fungal diseases is significantly less than that necessary for the antifungal alone, and will be about 5–14 days.

The following Examples serve to illustrate the invention. They are representative in nature and should not be construed in any way as narrowing or limiting the scope of the invention.

EXAMPLE 1

A. A cream having the following composition:

| Ingredients | Wt % |
|---|---|
| Water | qs |
| Glycerin | 5 |
| Glyceryl monostearate, self emulsifying type | 3 |
| Triethanolamine | 0.5 |
| White petrolatum | 4 |
| Propylene glycol | 10 |
| Propylene glycol dicaprylate | 5 |
| Cetyl alcohol | 6 |
| Stearic acid | 5 |
| Polyolprepolymer-2 | 1 |
| Polyoxyethylene (23) cetyl ether | 4 |
| Benzyl alcohol | 1 |
| Sodium benzoate | 0.2 |
| Betamethasone dipropionate | 0.064 |
| Butenafine hydrochloride | 1 | was prepared in the following manner:

Into a suitable vessel for holding the water phase, the water was added, followed by the glycerin, triethanolamine, and sodium benzoate with mixing while heating to about 80° C. Into a second vessel suitable for holding the oil phase, a mixture of the white petrolatum, cetyl alcohol, stearic acid, polyoxyethylene (23) cetyl ether, glyceryl monostearate SE, propylene glycol dicaprylate, propylene glycol, and polyolprepolymer-2 were heated to about 80° C. to melt while mixing continuously until uniform. The betamethasone dipropionate was then added to the oil phase and mixed until dissolved, followed by the butenafine HCl, which was also mixed until dissolved. While maintaining the temperature, the oil phase was added to the water phase while mixing. The mixture was cooled to about 50° C. with mixing, then benzyl alcohol was added and mixing continued until uniform. The mixture was then placed under a homogenizer and mixed until smooth and uniform. Mixing was continued with a stirrer at low speed while cooling the mixture to room temperature, giving the desired cream.

B. Similarly, a cream was prepared with the above proportions except that triethanolamine 0.5% was replaced by diethanolamine 0.5%.

EXAMPLE 2

A. A cream having the following composition:

| Ingredients | Wt % |
| --- | --- |
| Water | qs |
| Glycerin | 5 |
| Glyceryl monostearate, self emulsifying type | 5 |
| Triethanolamine | 0.3 |
| White petrolatum | 4 |
| Propylene glycol | 7 |
| Propylene glycol dicaprylate | 10 |
| Cetyl alcohol | 4 |
| Stearic acid | 3 |
| Polyoxyethylene (23) cetyl ether | 2 |
| Benzyl alcohol | 1 |
| Sodium benzoate | 0.2 |
| Betamethasone dipropionate | 0.064 |
| Butenafine hydrochloride | 1 | was prepared as shown in Example 1.

B. Similarly, a cream was prepared with the above proportions except that triethanolamine 0.3% was replaced by diethanolamine 0.3% and sodium benzoate was removed.

EXAMPLE 3

A. A cream having the following composition:

| Ingredients | Wt % |
| --- | --- |
| Water | qs |
| Glycerin | 5 |
| Glyceryl monostearate, self emulsifying type | 5 |
| Diethanolamine | 0.3 |
| White petrolatum | 4 |
| Propylene glycol | 7 |
| Propylene glycol dicaprylate | 10 |
| Cetyl alcohol | 4 |
| Stearic acid | 3 |
| Polyolprepolymer-2 | 1 |
| Polyoxyethylene (23) cetyl ether | 2 |
| Benzyl alcohol | 1 |
| Sodium benzoate | 0.2 |
| Betamethasone dipropionate | 0.064 |
| Butenafine hydrochloride | 1 | was prepared as shown in Example 1.

B. Similarly, a cream was prepared with the above proportions except that diethanolamine 0.3% was replaced by triethanolamine 0.3%.

EXAMPLE 4

A. A cream having the following composition:

| Ingredients | Wt % |
| --- | --- |
| Water | qs |
| Glycerin | 5 |
| Glyceryl monostearate, self emulsifying type | 3 |
| Triethanolamine | 0.5 |
| White petrolatum | 4 |
| Propylene glycol | 10 |
| Propylene glycol dicaprylate | 5 |
| Cetyl alcohol | 6 |
| Stearic acid | 5 |
| Polyoxyethylene (23) cetyl ether | 4 |
| Benzyl alcohol | 1 |
| Sodium benzoate | 0.2 |
| Betamethasone dipropionate | 0.064 |
| Butenafine hydrochloride | 1 | was prepared as shown in Example 1.

B. Similarly, a cream was prepared with the above proportions except that triethanolamine 0.5% was replaced by diethanolamine 0.5%.

EXAMPLE 5

A. A cream having the following composition:

| Ingredients | Wt % |
| --- | --- |
| Water | qs |
| Glycerin | 7 |
| Glyceryl monostearate, self emulsifying type | 4 |
| Triethanolamine | 0.3 |
| White petrolatum | 3 |
| Propylene glycol | 5 |
| Propylene glycol dicaprylate | 7 |
| Cetyl alcohol | 5 |
| Stearic acid | 4 |
| Polyolprepolymer-2 | 1 |
| Polyoxyethylene (23) cetyl ether | 3 |
| Benzyl alcohol | 1 |
| Sodium benzoate | 0.2 |
| Betamethasone dipropionate | 0.064 |
| Butenafine hydrochloride | 1 | was prepared as shown in Example 1.

B. Similarly, a cream was prepared with the above proportions except that triethanolamine 0.3% was replaced by diethanolamine 0.3%.

EXAMPLE 6

A. A cream having the following composition:

| Ingredients | Wt % |
| --- | --- |
| Water | qs |
| Glycerin | 7 |
| Glyceryl monostearate, self emulsifying type | 4 |
| Triethanolamine | 0.3 |
| White petrolatum | 3 |
| Propylene glycol | 5 |
| Propylene glycol dicaprylate | 7 |
| Cetyl alcohol | 5 |
| Stearic acid | 4 |
| Polyoxyethylene (23) cetyl ether | 3 |
| Benzyl alcohol | 1 |
| Sodium benzoate | 0.2 |
| Betamethasone dipropionate | 0.064 |
| Butenafine hydrochloride | 1 | was prepared as shown in Example 1.

B. Similarly, a cream was prepared with the above proportions except that triethanolamine 0.3% was replaced by diethanolamine 0.3%.

EXAMPLE 7

A cream having the following composition was prepared.

| Ingredients | Wt % |
| --- | --- |
| Water | qs to 100% |
| White petrolatum | 8 |
| Propylene glycol | 3 |
| Cetearyl alcohol | 6 |
| Polyolprepolymer-2 | 1 |
| Stearic Acid | 4 |
| Mineral oil | 8 |
| Ceteareth-30 | 8 |
| Dibasic sodium phosphate | 0.5 |
| Phosphoric acid | 0.02 |
| Benzyl alcohol | 1 |
| Betamethasone dipropionate | 0.064 |
| Butenafine HCl | 1 |

The dibasic sodium phosphate was dissolved in the water and phosphoric acid was added. The white petrolatum, cetearyl alcohol, stearic acid, ceteareth-30, mineral oil, polyolrepolymer-2, and propylene glycol were heated to melt with mixing until uniform. The betamethasone dipropionate and butenafine HCl were then dissolved in the oil phase, and the oil phase then added to the water phase with mixing. The batch was allowed to cool to about 50° C. and benzyl alcohol was added. The batch was homogenized until smooth and uniform and allowed to cool to room temperature with mixing.

EXAMPLE 8

An ointment having the following composition was prepared.

| Ingredients | Wt % |
| --- | --- |
| White petrolatum | qs to 100% |
| Propylene glycol | 20 |
| Glyceryl stearate | 3 |
| Betamethasone dipropionate | 0.064 |
| Butenafine HCl | 1 |

The glyceryl stearate and white petrolatum were melted by heating to about 65° C. with mixing. The butenafine HCl and betamethasone dipropionate were dissolved in the propylene glycol with heating to about 65° C. and then added to the melted glyceryl stearate and white petrolatum mixture with mixing. The mixture was allowed to cool to room temperature with continuous mixing.

EXAMPLE 9

A gel having the following composition was prepared.

| Ingredients | Wt % |
| --- | --- |
| Water | qs to 100% |
| Ethanol | 48 |
| Propylene glycol | 10 |
| Glycerin | 5 |
| Polyolprepolymer-2 | 1 |
| Hydroxypropyl cellulose | 1.8 |
| Betamethasone dipropionate | 0.064 |
| Butenafine HCl | 1 |

The butenafine HCl was dissolved in the ethanol, followed by betamethasone dipropionate. The polyethylene glycol 400, propylene glycol, glycerin, and polyolprepolymer-2 were then added and mixed until dissolved and uniform. Water was then added and mixed until uniform. If necessary, the base or the buffer (in solution) was added to the above solution with mixing to achieve the desired pH. The hydroxypropyl cellulose was then dispersed into the solution.

EXAMPLE 10

A lotion having the following composition is prepared.

| Ingredients | Wt % |
| --- | --- |
| Water | qs to 100% |
| Propylene glycol | 3 |
| Glycerin | 5 |
| Propylene glycol dicaprylate | 3 |
| Glyceryl monostearate, self emulsifying type | 2 |
| Polyoxyethylene cetyl ether | 2 |
| Stearic acid | 2 |
| Cetyl alcohol | 0.5 |
| White petrolatum | 1 |
| Polyolprepolymer-2 | 3 |
| Benzyl alcohol | 1 |
| Sodium benzoate | 0.2 |
| Magnesium aluminum silicate | 0.4 |
| Xanthan gum | 0.25 |
| Triethanolamine | 0.3 |
| Betamethasone dipropionate | 0.064 |
| Butenafine HCl | 1 |

Mix the magnesium aluminum silicate and xanthan gum and disperse into the water using a homogenizer. Add the glycerin to the above water phase and heat to 70 to 80° C. with mixing. Into another vessel for holding the oil phase, add the propylene glycol dicaprylate, propylene glycol, glyceryl monostearate SE, cetyl alcohol, white petrolatum, stearic acid, polyoxyethylene (23) cetyl ether, polyolprepolymer-2. Heat to 70 to 80° C. with mixing until melted and uniform. Add the betamethasone dipropionate and mix until dissolved followed by butenafine HCl. Maintain temperature and add the oil phase to the water phase with mixing. Dissolve the triethanolamine and sodium benzoate in the remaining water and add to the batch with mixing. Cool the batch to about 50° C. and add the benzyl alcohol. Homogenize the batch and then allow to cool to room temperature with mixing. A lotion having the following composition is prepared.

EXAMPLE 11

A liquid solution having the following composition was prepared.

| Ingredients | Wt % |
| --- | --- |
| Water | qs to 100% |
| Ethanol | 48 |
| Polyethylene glycol 400 | 5 |
| Propylene glycol | 10 |
| Glycerin | 5 |
| Polyolprepolymer-2 | 1 |
| Betamethasone dipropionate | 0.064 |
| Butenafine HCl | 1 |

The butenafine HCl was dissolved in the ethanol, followed by betamethasone dipropionate. The polyethylene glycol 400, propylene glycol, glycerin, and polyolprepolymer-2 were then added and mixed until dissolved and uniform. Water was added, and mixed until uniform. The pH of the solution was 4.4. Triethanolamine (TEA) can be added to further increase the pH if necessary. For example, 0.05 g of TEA in 100 g of solution would bring the pH to 5.1 whereas 0.1 g of TEA would give a pH of 5.6.

EXAMPLE 12

Comparison of Antifungal/Steroid Mixture Versus Antifungal and Vehicle

Subjects with tinea pedis were randomly assigned to treatment for seven days with 1) butenafine hydrochloride 1%/betamethasone dipropionate 0.064% cream; 2) butenafine hydrochloride 1% cream; or 3) placebo (vehicle).

The following efficacy variables were derived from the mycological and clinical responses to treatment on days 8, 14 and 49.

| | MYCOLOGICAL CURE RATES | | |
| --- | --- | --- | --- |
| Day | Butenafine plus Betamethasone | Butenafine | Vehicle |
| 8 | 72% | 52% | 23% |
| 14 | 68% | 48% | 25% |
| 49 | 72% | 71% | 37% |

The mycological cure rate is derived from a negative KOH wet mount and negative culture for a dermatophyte.
It can be seen that the rate of cure for the butenafine/betamethasone group reached a maximum at day 8, whereas butenafine alone does not approach this efficiency until day 49.

| | EFFECTIVE TREATMENT RATES | | |
| --- | --- | --- | --- |
| Day | Butenafine plus Betamethasone | Butenafine | Vehicle |
| 8 | 28% | 7% | 7% |
| 14 | 24% | 14% | 14% |
| 49 | 72% | 42% | 18% |

The effective treatment cure rate is derived from the mycological cure rate and an investigator global assessment of either "excellent" or "cleared".

Effective treatment cure rates were significantly higher for the butenafine/betamethasone group, especially at day 8.

| | OVERALL CURE RATES | | |
| --- | --- | --- | --- |
| Day | Butenafine plus Betamethasone | Butenafine | Vehicle |
| 8 | 4% | 0% | 0% |
| 14 | 4% | 4% | 0% |
| 49 | 28% | 18% | 0% |

The overall cure rate is derived from mycological cure rate and an investigator global assessment of "cleared".

Overall cure rates were significantly higher for the butenafine/betamethasone group, especially at day 49.

It can be therefore be seen that 6 weeks after therapy has finished, the butenafine/betamethasone combination continues to provide more complete symptom relief than butenafine alone.

EXAMPLE 13

Comparison of Antifungal/Steroid Mixture Versus Lotrisone

The purpose of this in vitro study was to determine the percutaneous absorption of butenafine and betamethasone diproprionate (BMD) using dual label methodology. Marketed product, Lotrisone®, served as control for BMD delivery.

A clinically relevant dose of the test formulation (5 mg/cm$^2$) was applied to dermatomed human skin mounted on flow-through diffusion cells. The receptor fluid, PBS containing 0.01% sodium azide and 1.5% Oleth, was collected at 6 hour intervals. After a 24 hour exposure period, the surface material was removed from the skin by two dry wipes followed by a single tape-strip. The epidermis was then separated from the dermis of each skin sample prior to analysis by Liquid Scintillation Counting.

The test formulations significantly exceeded Lotrisone with respect to epidermal deposition of BMD, but penetration of the epidermis by BMD in the Lotrisone formulation proved to be significantly higher than that shown for the formulations of the present invention.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A topical antifungal composition comprising:
   a) a therapeutically effective amount of an antifungal compound of the formula:

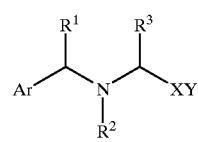

wherein:
$R^1$, $R^2$, and $R^3$ are independently hydrogen or lower alkyl;
X is —$(CH_2)_n$—;

in which n is 0, 1 or 2;

Y is —C≡C—R$^4$, or aryl;

in which R$^4$ is lower alkyl; and

Ar is aryl;

or a pharmaceutically acceptable salt thereof;

b) a therapeutically effective amount of an antiinflammatory steroid; and c) pharmaceutically acceptable excipients sufficient to form a topical composition.

2. The composition of claim 1, wherein the therapeutically effective amount of the antifungal compound is an amount between about 0.5% and 5% by weight of the total composition and the therapeutically effective amount of the antiinflammatory steroid is an amount between about 0.001% and 2.5% by weight of the total composition.

3. The composition of claim 2, wherein the composition is formulated as a cream, ointment, gel, lotion, foam, powder, aerosol, spray, shampoo, or liquid solution.

4. The composition of claim 3, wherein the composition is a cream.

5. The composition of claim 4 having a pH of about 3.5 to about 7.0, wherein the pharmaceutically acceptable excipients comprise:

at least one solvent, at least one emollient, at least one humectant, at least one preservative, and at least one emulsifier; and optionally including an acid, base, or buffering agent to adjust the pH.

6. The composition of claim 5, wherein:

the solvent is chosen from one or more of propylene glycol, butylene glycol, hexylene glycol, polyethylene glycols, polypropylene glycols, and polyurethane compounds;

the emollient is chosen from one or more of white petrolatum, mineral oil, propylene glycol dicaprylate, lower fatty acid esters and lower alkyl ethers of propylene glycol, cetyl alcohol, cetostearyl alcohol, stearyl alcohol, stearic acid, cetyl esters wax, spermaceti wax, and white wax;

the humectant is chosen from glycerin and sorbitol; and the emulsifier is chosen from one or more of glyceryl monostearate, glyceryl monoleate, stearic acid, polyoxyethylene cetyl ether, polyoxyethylene cetostearyl ether, polyoxyethylene stearyl ether, and polyethylene glycol stearate;

wherein the optional acid is chosen from hydrochloric acid and phosphoric acid, the optional base is chosen from diethanolamine, triethanolamine, and sodium hydroxide, the optional buffering agent is chosen from monobasic sodium phosphate and dibasic sodium phosphate, and the preservative is chosen from benzyl alcohol, sodium benzoate and parabens.

7. The composition of claim 6, wherein the antiinflammatory steroid is betamethasone, betamethasone dipropionate, fluocinonide, fluocinoline acetonide, hydrocortisone, methylprednisolone, clobetasol, or beclomethasone.

8. The composition of claim 7, wherein a solvent is a hydroxy-terminated polyurethane compound chosen from polyolprepolymer-2, polyolprepolymer-14, and polyolprepolymer-15.

9. The composition of claim 8, wherein Ar is optionally substituted naphthyl, R$^1$ and R$^3$ are hydrogen, and R$^2$ is methyl.

10. The composition of claim 9, wherein Y is optionally substituted phenyl or —C≡C—R$^4$.

11. The composition of claim 10, wherein Ar is 1-naphthyl, n is 0, and Y is 4-t-butylphenyl or a pharmaceutically acceptable salt thereof.

12. The composition of claim 10, wherein the cream is:

| Ingredients | Wt % |
| --- | --- |
| Water | qs |
| Glycerin | 2–10 |
| Glyceryl monostearate, self emulsifying type | 1–10 |
| Triethanolamine | 0.1–1.0 |
| White petrolatum | 1–10 |
| Propylene glycol | 5–20 |
| Propylene glycol dicaprylate | 5–20 |
| Cetyl alcohol | 1–10 |
| Stearic acid | 1–10 |
| Polyolprepolymer-2 | 0–5 |
| Polyoxyethylene (23) cetyl ether | 1–10 |
| Benzyl alcohol | 0.5–3 |
| Sodium benzoate | 0–0.5 |
| Steroid | 0.01–2.5 |
| Antifungal | 0.5–5 |

13. The composition of claim 12, wherein the cream composition is:

| Ingredients | Wt % |
| --- | --- |
| Water | qs |
| Glycerin | 5 |
| Glyceryl monostearate, self emulsifying type | 3 |
| Triethanolamine | 0.5 |
| White petrolatum | 4 |
| Propylene glycol | 10 |
| Propylene glycol dicaprylate | 5 |
| Cetyl alcohol | 6 |
| Stearic acid | 5 |
| Polyolprepolymer-2 | 1 |
| Polyoxyethylene (23) cetyl ether | 4 |
| Benzyl alcohol | 1 |
| Sodium benzoate | 0.2 |
| Betamethasone dipropionate | 0.064 |
| Butenafine hydrochloride | 1 |

14. The composition of claim 12, wherein the cream composition is:

| Ingredients | Wt % |
| --- | --- |
| Water | qs |
| Glycerin | 5 |
| Glyceryl monostearate, self emulsifying type | 5 |
| Triethanolamine | 0.3 |
| White petrolatum | 4 |
| Propylene glycol | 7 |
| Propylene glycol dicaprylate | 10 |
| Cetyl alcohol | 4 |
| Stearic acid | 3 |
| Polyoxyethylene (23) cetyl ether | 2 |
| Benzyl alcohol | 1 |
| Sodium benzoate | 0.2 |
| Betamethasone dipropionate | 0.064 |
| Butenafine hydrochloride | 1 |

15. The composition of claim 12, wherein the cream composition is:

16. The composition of claim 12, wherein the cream composition is:

| Ingredients | Wt % |
| --- | --- |
| Water | qs |
| Glycerin | 5 |
| Glyceryl monostearate, self emulsifying type | 5 |
| Triethanolamine | 0.3 |
| White petrolatum | 4 |
| Propylene glycol | 7 |
| Propylene glycol dicaprylate | 10 |
| Cetyl alcohol | 4 |
| Stearic acid | 3 |
| Polyolprepolymer-2 | 1 |
| Polyoxyethylene (23) cetyl ether | 2 |
| Benzyl alcohol | 1 |
| Sodium benzoate | 0.2 |
| Betamethasone dipropionate | 0.064 |
| Butenafine hydrochloride | 1 |

17. The composition of claim 12, wherein the cream composition is:

| Ingredients | Wt % |
| --- | --- |
| Water | qs |
| Glycerin | 5 |
| Glyceryl monostearate, self emulsifying type | 3 |
| Triethanolamine | 0.5 |
| White petrolatum | 4 |
| Propylene glycol | 10 |
| Propylene glycol dicaprylate | 5 |
| Cetyl alcohol | 6 |
| Stearic acid | 5 |
| Polyoxyethylene (23) cetyl ether | 4 |
| Benzyl alcohol | 1 |
| Sodium benzoate | 0.2 |
| Betamethasone dipropionate | 0.064 |
| Butenafine hydrochloride | 1 |

18. The composition of claim 12, wherein the cream composition is:

| Ingredients | Wt % |
| --- | --- |
| Water | qs |
| Glycerin | 7 |
| Glyceryl monostearate, self emulsifying type | 4 |
| Triethanolamine | 0.3 |
| White petrolatum | 3 |
| Propylene glycol | 5 |
| Propylene glycol dicaprylate | 7 |
| Cetyl alcohol | 5 |
| Stearic acid | 4 |
| Polyolprepolymer-2 | 1 |
| Polyoxyethylene (23) cetyl ether | 3 |
| Benzyl alcohol | 1 |
| Sodium benzoate | 0.2 |
| Betamethasone dipropionate | 0.064 |
| Butenafine hydrochloride | 1 |

| Ingredients | Wt % |
| --- | --- |
| Water | qs |
| Glycerin | 7 |
| Glyceryl monostearate, self emulsifying type | 4 |
| Triethanolamine | 0.3 |
| White petrolatum | 3 |
| Propylene glycol | 5 |
| Propylene glycol dicaprylate | 7 |
| Cetyl alcohol | 5 |
| Stearic acid | 4 |
| Polyoxyethylene (23) cetyl ether | 3 |
| Benzyl alcohol | 1 |
| Sodium benzoate | 0.2 |
| Betamethasone dipropionate | 0.064 |
| Butenafine hydrochloride | 1 |

19. The composition of claim 10, wherein the cream is:

| Ingredients | Wt % |
| --- | --- |
| Water | qs |
| White petrolatum | 1–20 |
| Propylene glycol | 2–20 |
| Cetearyl alcohol | 1–10 |
| Polyolprepolymer-2 | 0–3 |
| Stearic acid | 1–10 |
| Mineral oil | 5–20 |
| Ceteareth-30 | 1–10 |
| Benzyl alcohol | 0.5–3 |
| Steroid | 0.01–2.5 |
| Antifungal | 0.5–5 | wherein an acid or base is added in quantity sufficient to adjust the pH of the cream to about 3.5 to 7.0.

20. The composition of claim 19, wherein the antiinflammatory steroid is betamethasone dipropionate and the antifungal is butenafine hydrochloride.

21. The composition of claim 10, wherein the cream composition is:

| Ingredients | Wt % |
| --- | --- |
| Water | qs to 100% |
| White petrolatum | 8 |
| Propylene glycol | 3 |
| Cetearyl alcohol | 6 |
| Polyolprepolymer-2 | 1 |
| Stearic Acid | 4 |
| Mineral oil | 8 |
| Ceteareth-30 | 8 |
| Dibasic sodium phosphate | 0.5 |
| Phosphoric acid | 0.02 |
| Benzyl alcohol | 1 |
| Betamethasone dipropionate | 0.064 |
| Butenafine HCl | 1 |

22. The composition of claim 10, wherein the cream is:

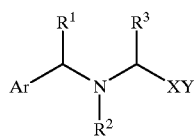

wherein an acid or base is added in quantity sufficient to adjust the pH of the cream to about 3.5 to 7.0.

23. The composition of claim 22, wherein the antiinflammatory steroid is betamethasone dipropionate and the antifungal is butenafine hydrochloride.

24. A method of treating a fungal disease, comprising application to the skin of a mammal in need of such treatment a topical composition comprising:
   a) an effective amount of an antifungal compound of the formula:

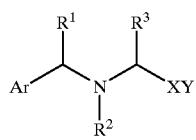

wherein:

$R^1$, $R^2$, and $R^3$ are independently lower alkyl;

X is $-(CH_2)_n-$;

in which n is 0, 1 or 2;

Y is $-C{\equiv}C-R^4$, or aryl;

in which $R^4$ is lower alkyl; and

Ar is aryl;

or a pharmaceutically acceptable salt thereof;

b) an effective amount of an antiinflammatory steroid;

c) amounts of pharmaceutically acceptable excipients sufficient to form a topical composition.

25. The fungal disease of claim 24 which is chosen from tinea pedis, tinea capitis, tinea corporis, tinea versicolor, nail fungal diseases, scalp disorders, tinea cruris, and candidiasis.

26. An article of manufacture, comprising:

(A) the topical composition of claim 1, in combination with:

(B) labeling instructions for application of said topical composition for the treatment of fungal diseases.

* * * * *